United States Patent [19]

Egbert

[11] 4,351,183

[45] Sep. 28, 1982

[54] APPARATUS AND METHOD FOR DETERMINING THE OSMOLARITY/SPECIFIC GRAVITY OF A SOLUTION

[76] Inventor: Bill R. Egbert, Rte. 5, P.O. Box 338, Blackfoot, Id. 83221

[21] Appl. No.: 202,408

[22] Filed: Oct. 31, 1980

[51] Int. Cl.³ .................. G01N 9/00; G01N 13/04
[52] U.S. Cl. .................................... 73/32 R; 73/64.3
[58] Field of Search ............... 73/32 R, 64.3; 422/56, 422/57, 68

[56] References Cited

U.S. PATENT DOCUMENTS

| | | | |
|---|---|---|---|
| 3,139,328 | 6/1964 | Jacob | 422/56 |
| 4,015,462 | 4/1977 | Greyson et al. | 73/32 R |
| 4,046,514 | 9/1977 | Johnston et al. | 422/56 |
| 4,205,043 | 5/1980 | Esch | 422/56 |

Primary Examiner—James J. Gill
Attorney, Agent, or Firm—H. Ross Workman; Allen R. Jensen; J. Winslow Young

[57] ABSTRACT

A novel apparatus and method for determining osmolarity and/or specific gravity of a sample solution, the apparatus including a plurality of test solutions, each test solution having a predetermined specific gravity within a predetermined specific gravity range and also containing the dye, the dye being activated by substances in the sample solution. Test solutions having a higher specific gravity than the sample solution will experience osmotic diffusion across the semipermeable membrane and activation of the dye therein. The test solutions are sequentially arrayed on a support member so that the next succeeding test solution without a color change indicates the degree of osmolarity and/or specific gravity of the sample solution.

10 Claims, 4 Drawing Figures

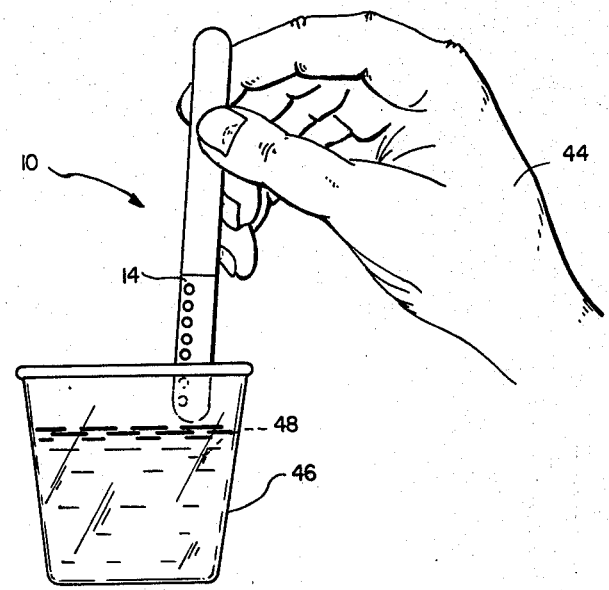
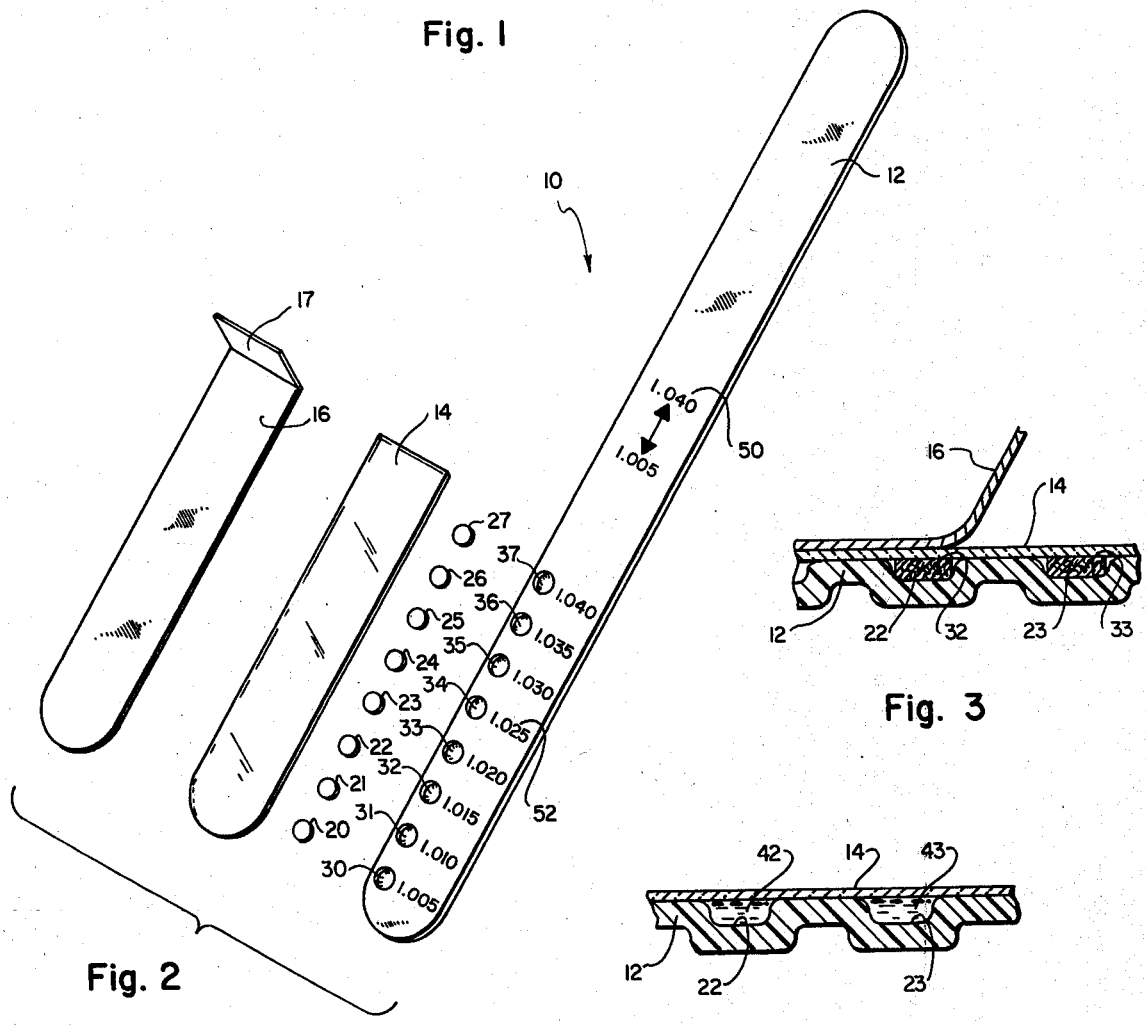
Fig. 1
Fig. 2
Fig. 3
Fig. 4

APPARATUS AND METHOD FOR DETERMINING THE OSMOLARITY/SPECIFIC GRAVITY OF A SOLUTION

BACKGROUND

1. Field of the Invention

This invention relates to an apparatus and method for determining the osmolarity/specific gravity of a solution and, more particularly, through a novel system for matching the osmolarity of an unknown solution with one of a plurality of discrete test solutions of known concentrations encapsulated with a semipermeable membrane.

2. The Prior Art

The determination of the osmolarity and/or specific gravity of a sample solution is an important analytical procedure for many applications. Various methods and apparatus for measuring osmolarity and/or specific gravity of a solution are commercially available and well-known in the art. Available apparatus include hydrometers, gravitometers, pycnometers, urinometers, and osmometers. While these devices are generally conceded to be accurate, they also tend to be expensive, bulky, and generally require a substantial investment in operator time, support equipment, supplies, calibration, and, in certain instances, a relatively large liquid sample volume.

A recent prior art device is disclosed in U.S. Pat. No. 4,015,462 issued Apr. 5, 1977 and relates to a system incorporating a plurality of osmotically fragile, semipermeable membrane capsules having a predetermined specific gravity and containing a combination of solute and coloring substance. Contact between the test system and a liquid having a specific gravity lower than the specific gravity of the test system produces the hydrostatic pressure within the capsules causing the capsules to break and release the coloring substance. The density of the color produced by the release of the coloring substance is inversely related to and indicative of the specific gravity of the liquid contacted. This test system requires the evaluation of the intensity of the color with a color standard in order to determine specific gravity and is, therefore, subject to variation depending upon the particular individual making the intensity determination.

In view of the foregoing, it would be an advancement in the art to provide a novel test apparatus and method for determining the osmolarity/specific gravity of a solution that is accurate, easily readable even by an unskilled operator, and rapid without the requirement for expensive, bulky or otherwise difficult to calibrate equipment, and the like. It would also be an advancement in the art to provide a single-use test apparatus and method for determining the osmolarity/specific gravity of a solution wherein the apparatus is inexpensive and readily disposable. Such an invention is disclosed and claimed herein.

BRIEF SUMMARY AND OBJECTS OF THE INVENTION

The present invention relates to a novel test apparatus and method for determining the osmolarity/specific gravity of a sample solution, the apparatus including a plurality of dye-containing test solutions of known specific gravity covered by a semipermeable membrane. The range of specific gravity values of the test samples are preselected to extend through the anticipated range of specific gravity values to be encountered in a sample solution. The dye in the test samples is selectively predetermined so as to be activated upon contact with a known substance such as a known solute or ion in the sample solution. The semipermeable membrane is chosen such that osmotic diffusion will carry at least some of the solute or ion from the sample solution into one or more of the test solutions thereby activating the dye and causing a color change to occur. The absence of color change will indicate the lack of osmotic diffusion across the semipermeable membrane thereby providing an indication of a balancing of the specific gravity and/or osmolarity between the test sample solution and the respective test solutions.

It is, therefore, a primary object of this invention to provide improvements in apparatus for determining the osmolarity/specific gravity of a sample solution.

Another object of this invention is to provide an improved method for determining the osmolarity/specific gravity of a sample solution.

Another object of this invention is to provide an apparatus for determining the osmolarity/specific gravity of a sample solution by (1) exposing (across a semipermeable membrane) a plurality of dye-containing, test solutions of known specific gravity within a predetermined specific gravity range so that (2) at equilibrium between the specific gravities of the two solutions (as determined by the lack of color change in the dye) (3) an indication of the specific gravity of the sample solution will be obtained.

These and other objects and features of the present invention will become more fully apparent from the following description and appended claims taken in conjunction with the accompanying drawing.

BRIEF DESCRIPTION OF THE DRAWING

FIG. 1 is a schematic illustration of the novel test apparatus of this invention shown in the environment of a sample solution;

FIG. 2 is an exploded, enlarged perspective view of the novel test apparatus of FIG. 1;

FIG. 3 is an enlarged, partial cross-sectional view of the assembled test apparatus of FIG. 2; and FIG. 4 is an enlarged, cross-sectional view of a second preferred embodiment of the novel test apparatus of this invention.

DETAILED DESCRIPTION OF THE PREFERRED EMBODIMENTS

The invention is best understood by reference to the drawing wherein like parts are designated with like numerals throughout.

GENERAL DISCUSSION

Osmolarity is defined as the total number of particles of solute or solutes in a solution of specific volume. Correspondingly, specific gravity is defined as the weight per unit volume of a liquid or solution as compared with water of an equal volume, water being given a unit value of 1.000. Accordingly, if the ionization of a solute and its molecular weight are taken into account, the specific gravity of the resulting solution can be calculated from the osmolarity which can be adjusted to be read as specific gravity.

In its most precise definition, a semipermeable membrane is a membrane that is permeable to the solvent but impermeable to the dissolved substances. However, most membranes are not truly semipermeable since an appreciable amount of solute will actually pass through the membrane along with some of the solvent. It is this characteristic that is advantageously utilized in the present invention to determine the osmolarity and, therefore, the specific gravity of a sample solution. In particular, a dye or color indicator is incorporated in a plurality of test solutions having different but predetermined concentrations or specific gravities. A semipermeable membrane separates each test solution from the sample solution. Osmotic diffusion through the semipermeable membrane carries both solvent and a portion of the solute into the respective test solutions, the solute activating the dye. The activation of the dye indicates that osmosis has occurred across the semipermeable membrane into the applicable test solutions of known concentrations.

However, when the specific gravity of the sample solution is nearly identical with the specific gravity of the test solution, the absence of osmotic diffusion will be indicated by a lack of color change within the particular test solution. Broadly stated, this lack of osmotic diffusion indicates that either (1) the two solutions are of identical or nearly identical specific gravities, or (2) that the specific gravity of the sample solution is higher than the specific gravity of the test solution. It is, therefore, necessary to sequentially arrange a plurality of test solutions having known concentrations or specific gravities within the expected range of the test sample so that the lack of color change adjacent the last test sample to change color will provide the appropriate indication.

As will be discussed more fully hereinafter, one presently preferred embodiment of the apparatus for carrying out the foregoing determination of osmolarity and/or specific gravity of a sample solution includes an immersible strip having a plurality of discrete compartments aligned thereon. Each of the compartments contains a quantity of dye-containing test solution having a predetermined specific gravity. The specific gravity of each of the test solutions falls within the preselected range at preselected intervals. The test solutions are arranged sequentially along the strip. Each of the compartments are covered with a semipermeable membrane. Osmotic diffusion will occur across the semipermeable membrane during immersion. Solvent and some solute in the sample solution will pass into each of the test solutions having a greater specific gravity than the sample solution. Osmotic equilibrium will be indicated by the next succeeding test solution adjacent the last test solution to indicate color thereby providing a readily readable, relatively accurate apparatus and method for determining osmolarity and/or specific gravity of the test solution.

Referring now more particularly to FIG. 2, the novel apparatus of this invention is shown herein as a dipstick 10 including a support strip 12 having a plurality of cavities 30–37 formed therein. A semipermeable membrane 14 is adapted to sealingly cover each of cavities 30–37. A plurality of absorbent inserts 20–27 are provided an can be placed in each of cavities 30–37, respectively, the purpose of which will be discussed more fully hereinafter. A protective cover 16 is configured to be releasably sealed over semipermeable membrane 14 to thereby protect semipermeable membrane 14 from moisture, damage, and also insures against evaporation of the test solutions in cavities 30–37 through semipermeable membrane 14.

Support strip 12 is preferably fabricated from a relatively thin strip of white or other suitably colored plastic material having the desired strength characteristics. The color of support strip 12 is selectively predetermined to assist in the observation of color changes which occur during use of dipstick 10. For example, white is generally considered to be the most desirable color since white will accentuate most color changes within cavities 30–37. In one presently preferred embodiment of the novel dipstick 10 of this invention, a white plastic material for support strip 12 was fabricated from polyvinylchloride having a thickness of 5 mils, a width of about 6.5 mm and a length of about 127 mm. Importantly, the length of support strip 12 should be adequate to readily accommodate dipstick 10 being easily held in a hand 44 and immersed in a sample solution 48 in container 46 (FIG. 1). Additionally, the material of construction of support strip 12 should be of sufficient rigidity to accommodate dipstick 10 being used in its intended and other applications, for example, as a stirrer, or the like.

Semipermeable membrane 14 may be of any suitable semipermeable membrane material that is sufficiently transparent while serving as a desired osmotic diffusion barrier. One suitable, commercially available semipermeable membrane is identified as the TECHNICON type C dialysis membrane and may be purchased from Alpkem of Glochamor, Oreg. Semipermeable membrane 14 is sealingly secured to support strip 12 over cavities 30–37 to thereby suitably retain the test solutions therein by sealingly enclosing the test solution in each of cavities 30–37.

Inserts 20–27 are configured from a suitable filter material and serve as absorbent inserts for the purpose of simplifying manufacture of dipstick 10. In particular, it is well-known that a drop of liquid will, through well-known surface tension phenomena, exhibit an upwardly extending, curvilinear surface which has been known to interfere with the manufacturing process. In particular, a liquid droplet placed in any one of cavities 30–37 has been found to have an upwardly extending surface resulting from the surface tension of the droplet with the effect that when semipermeable membrane 14 is placed thereover, the droplet immediately wets the surface of semipermeable membrane 14 beyond the periphery of cavities 30–37 with a resulting interference with the adhesion of semipermeable membrane 14 to the surrounding surface of support strip 12. Accordingly, each of inserts 20–27 is saturated with the desired test solution in cavities 30–37, thereby removing the tendency for the foregoing interference to occur.

The test solution for each of cavities 30–37 is selectively prepared to cover the predetermined specific gravity range for dipstick 10. In the illustrated embodiment, the test solutions are selectively predetermined to have a specific gravity range of 8 equal increments (see indicia 52) between a specific gravity of 1.005 and 1.040 (see indicia 52). In this particular instance, the test solutions are prepared from potassium chloride dissolved in a suitable dye such as chlorophosphonoazo III. Chlorophosphonoazo III is a well-known, commercially available, calcium indicator dye and may be obtained, for example, from Harleco Chemicals of Gibbstown, N.J. Advantageously, chlorophosphonoazo III is a stable dye in solution and is well-known for its characteristics of changing from a normally purple to a blue color in the presence of calcium ions. Another satisfactory dye for detecting the presence of calcium is known by the tradename CALCHROME-10B and is available from Oxford Laboratories. CALCHROME-10B has the advantage in that it turns from a dark blue to a bright red-orange in the presence of calcium.

Inserts 20-27 are punched from a suitable, calcium-free filter paper and inserted into cavities 30-37 to thereby act as an absorbent for the test solution placed in each of cavities 30-37. With particular reference to FIG. 3, inserts 22 and 23 are shown as saturated with the appropriate test solution and inserted in cavities 32 and 33, respectively. Semipermeable membrane 14 is sealingly secured to the support strip 12 while overlayment 16 is releasably sealed across semipermeable membrane 14 to provide the desired protection and evaporation-loss characteristics discussed hereinbefore.

Alternatively, and with particular reference to FIG. 4, inserts 20-27 may be dispensed with and the desired test solution, test solutions 42 and 43 may be placed in each of cavities 22 and 23, respectively, and sealingly enclosed therein by semipermeable membrane 14. In either embodiment, test solutions 42 and 43 are exposed to the appropriate sample solution 48 (FIG. 1) across semipermeable membrane 14 for the purposes set forth hereinbefore.

The appropriate specific gravity indication for each of cavities 30-37 is selectively predetermined and indicated by indicia 52 placed adjacent each of cavities 30-37. The overall specific gravity range of dipstick 10 is suitably indicated by indicia range 50 embossed on support strip 12 at a position not concealed by protective cover 16.

With particular reference also to FIG. 1, the novel dipstick 10 of this invention is utilized by the operator (shown schematically herein as hand 44) holding the upper end of support strip 12 and stripping protective cover 16 therefrom. Protective cover 16 includes a tab 17 to permit easy handgrasping and hand removal of protective cover 16 from its overlayment position on top of semipermeable membrane 14. With semipermeable membrane 14 exposed, dipstick 10 is immersed in the particular sample 48 within a sample container 46. After a brief immersion, dipstick 10 is removed from sample 48 and observed for color changes in each of cavities 30-37. Test solutions in each of cavities 30-37 which have a higher specific gravity than sample 48 will show a color change inside cavities 30-37 since osmotic diffusion will occur across semipermeable membrane 14 carrying with it some of the solutes in sample 48. Providing sample 48 has a specific gravity within the specific gravity range indicated by indicia 50, the test solution in cavities 30-37 most nearly identical to that of sample 48 will result in little or no color change. Accordingly, the operator (not shown) can readily make a simple visual observation to obtain a determination of the specific gravity of sample solution 48 within a suitable margin of error for the particular sample being tested. Clearly, while the more precise explanation of the foregoing phenomena would be directed toward a system for testing osmolarity of a solution, it is the absence of osmotic diffusion that is detected and directly correlated as a comparison between the specific gravity of the test solution and the sample solution.

The Method

In one test of the method of this invention, chlorophosphonoazo III was divided into 10 aliquots of 5 milliliters each and the specific gravity of each aliquot was adjusted using potassium chloride to provide a specific gravity range from 1.000 to 1.045 at increments of 0.005 units each. Approximately five drops of each test solution were placed in individual test tubes and the mouth of each test tube was closed with a semipermeable membrane. A urine specimen believed to have a specific gravity within the range of 1.0002 to 1.045 was obtained and the ten test tubes were inverted into the urine specimen. It was found that sufficient color change occured in each of the test tubes containing solutions having a specific gravity greater than that of the urine so that the specific gravity of the urine could be determined within 0.005 units of the specific gravity measured on a conventional refractometer.

In place of the foregoing test tubes, the test solutions having the predetermined specific gravity range may be placed in each of cavities 30-37 and, where appropriate, absorbed into inserts 20-27 and sealingly enclosed by semipermeable membrane 14. Thereafter, protective cover 16 is applied as an overlayment across semipermeable membrane 14. Dipstick 10 is used as indicated previously to accommodate the novel features of the present apparatus and method of this invention.

While each of the foregoing dyes are directed toward a dye that is activated by a calcium ion, other well-known dyes may be suitably incorporated into the apparatus and method of this invention for the particular purposes set forth herein. For example, the detection of glucose or sucrose may be accomplished by using orthotoluidine which is a well-known dye used in the industry for detecting sucrose.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for determining the specific gravity or osmolarity of a sample solution comprising:
   support means;
   a plurality of test solutions, each test solution having a known and predetermined specific gravity; and
   semipermeable membrane means for sealingly enclosing each of the test solutions on the support means so that reaction of a test solution with a constituent of the sample solution in the area enclosed within the semipermeable membrane indicates that osmotic diffusion has occurred through the semipermeable membrane.

2. The apparatus defined in claim 1 wherein the semipermeable membrane further comprises a protective strip removably sealed over the semipermeable membrane.

3. The apparatus defined in claim 1 wherein the test solutions comprise dye means for imparting a distinctive color in the presence of substances from the sample solution.

4. The apparatus defined in claim 3 wherein the dye means comprises a calcium indicator dye selected from the group consisting of chlorophosphonoazo III and CALCHROME-10B.

5. The apparatus defined in claim 4 wherein the plurality of test sample solutions are deposited into at least eight separate compartments containing the test solutions having specific gravity values ranging between 1.005 and 1.040 at increments of 0.005.

6. The apparatus defined in claim 1 wherein the test sample solutions are absorbed into an absorbent medium.

7. Test means for determination of specific gravity or osmolarity of a sample solution comprising:
   a support means;
   a plurality of cavities in the support means;
   a plurality of test solutions placed in each of the cavities, each test solution having a predetermined specific gravity within a predetermined specific gravity range;
   indicator means in each of the test solutions, the indicator means being operable to selectively indicate the presence of substances from the sample solution; and
   semipermeable membrane means for sealingly enclosing each of the test solutions and the dye means on each of the cavities on the support means, the semipermeable membrane means being operable to accommodate osmotic diffusion of substances from a sample solution into test solutions in each of the cavities wherein the respective test solutions have a higher specific gravity than the sample solution, the osmotic diffusion of substances from the sample solution activating the dye in the test solution.

8. The apparatus defined in claim 7 wherein the semipermeable membrane means further comprises a protective cover sealingly and releasably enclosing the semipermeable membrane means to preclude evaporation of the test solutions in each of the cavities through the semipermeable membrane means.

9. The apparatus defined in claim 7 wherein each of said cavities comprises an absorbent filler for absorbing said test solutions in said cavities and thereby serving as a carrier for said test solutions.

10. A method for determining specific gravity or osmolarity of a liquid comprising:
    sealingly enclosing with a semipermeable membrane means, a plurality of discrete bodies of test solutions, each test solution having a predetermined specific gravity and a dye indicator means for indicating a color change upon passage of substances from the sample solution into the test solution;
    immersing the semipermeable membranes and sealingly enclosed test solutions into a sample solution thereby allowing substances from the sample solution to osmotically diffuse across the semipermeable membrane into test solutions having a higher specific gravity than the sample solution, substances from the sample solution causing a color change within the test solution; and
    visually observing the test solutions through the semipermeable membrane thereby comparing color changes of the test solutions as a function of osmolarity between the test solutions and the sample solution.

* * * * *